United States Patent
Matsumasa et al.

(10) Patent No.: US 9,801,036 B2
(45) Date of Patent: Oct. 24, 2017

(54) INITIAL RESCUE INFORMATION COLLECTION DEVICE, OPERATION METHOD THEREOF, RECORDING MEDIUM, AND SYSTEM

(71) Applicant: FUJIFILM Corporation, Tokyo (JP)

(72) Inventors: Hironori Matsumasa, Tokyo (JP); Satoshi Ueda, Tokyo (JP); Yasunori Ohta, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/184,658

(22) Filed: Jun. 16, 2016

(65) Prior Publication Data

US 2017/0034682 A1    Feb. 2, 2017

(30) Foreign Application Priority Data

Jul. 29, 2015   (JP) ................. 2015-150127

(51) Int. Cl.
   *H04M 11/04*    (2006.01)
   *H04W 4/22*     (2009.01)
   (Continued)

(52) U.S. Cl.
   CPC ............ *H04W 4/22* (2013.01); *G06F 19/327* (2013.01); *G06Q 10/06* (2013.01); *G08B 21/02* (2013.01);
   (Continued)

(58) Field of Classification Search
   None
   See application file for complete search history.

(56) References Cited

U.S. PATENT DOCUMENTS

2008/0004904 A1* 1/2008 Tran ................. A61B 5/0006
                                                      705/2
2008/0284587 A1* 11/2008 Saigh ............... H04M 1/72541
                                                   340/539.13
(Continued)

FOREIGN PATENT DOCUMENTS

JP    2015-32060 A    2/2015

OTHER PUBLICATIONS

Extended European Search Report dated Jul. 27, 2016 in corresponding Application No. 16 17 3280.5.

*Primary Examiner* — Idowu O Osifade
(74) *Attorney, Agent, or Firm* — Birch, Stewart, Kolasch & Birch, LLP

(57) ABSTRACT

An initial rescue information collection server includes a request receiving unit, a rescue request notification transmission unit, and a timeline processing unit. The request receiving unit receives a rescue request from a rescue requester who has sent the rescue request. The rescue request notification transmission unit selects users present in the vicinity of the rescue requester, and transmits a rescue request notification to the selected users. The request receiving unit receives initial rescue information from the selected users. The timeline processing unit generates a timeline in which the received initial rescue information is recorded in time series. Before emergency personnel arrive, the initial rescue information regarding the rescue requester is obtained by the rescuer. Therefore, it is easy to estimate the onset time or to check temporal changes in a condition.

19 Claims, 14 Drawing Sheets

(51) Int. Cl.
*G06F 19/00* (2011.01)
*G06Q 10/06* (2012.01)
*G08B 27/00* (2006.01)
*H04M 1/725* (2006.01)
*H04M 3/51* (2006.01)
*H04W 4/02* (2009.01)
*H04W 68/00* (2009.01)
*G08B 21/02* (2006.01)

(52) U.S. Cl.
CPC ........... *G08B 27/00* (2013.01); *G08B 27/001* (2013.01); *H04M 1/72536* (2013.01); *H04M 3/5116* (2013.01); *H04W 4/02* (2013.01); *H04W 68/005* (2013.01)

(56) References Cited

U.S. PATENT DOCUMENTS

| | | |
|---|---|---|
| 2011/0117878 A1 | 5/2011 | Barash et al. |
| 2015/0199895 A1 | 7/2015 | Hilliges et al. |
| 2016/0147941 A1 | 5/2016 | Ueda et al. |

\* cited by examiner

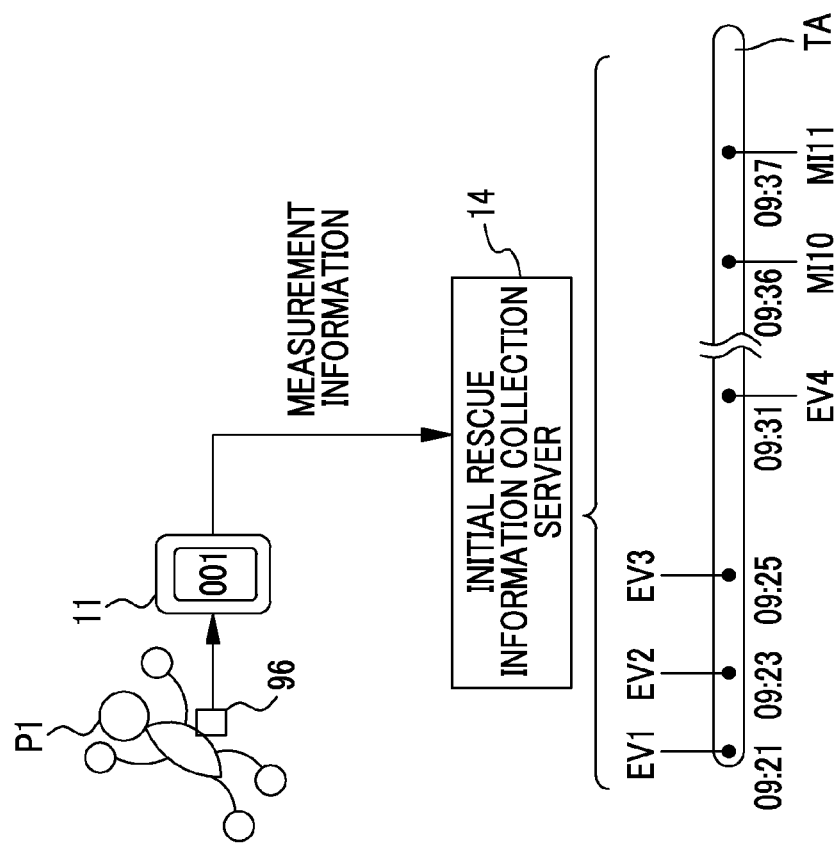

INITIAL RESCUE INFORMATION COLLECTION DEVICE, OPERATION METHOD THEREOF, RECORDING MEDIUM, AND SYSTEM

CROSS-REFERENCE TO RELATED APPLICATIONS

The present application claims priority under 35 U.S.C. §119 to Japanese Patent Application No. 2015-150127, filed on Jul. 29, 2015, all of which are hereby expressly incorporated by reference into the present application.

BACKGROUND OF THE INVENTION

1. Field of the Invention

The present invention relates to an initial rescue information collection device, an operation method thereof, a non-transitory computer readable computer medium storing a program, and a system.

2. Description of the Related Art

A medical assistance device is known that records, as a timeline, medical procedures performed on a rescue requester by emergency personnel, who are healthcare workers, in the emergency stage before the rescue requester is transported to a hospital after the emergency personnel arrive in the field of emergency where the rescue requester is present (for example, refer to JP2015-32060A). Here, the timeline refers to information in a format in which information regarding the rescue requester, such as procedures performed on the rescue requester, is recorded in time series.

In the medical assistance device disclosed in JP2015-32060A, in the emergency stage, triage treatment, measurement of vital signs, and the like are performed for a patient by emergency personnel. In addition, the condition of a patient, such as the condition of the external appearance of a patient, is recorded through photographing or the like. Such information regarding a patient is recorded in the timeline in the emergency stage. The timeline is registered, for example, in a medical assistance server installed in a fire command center to direct the dispatch of emergency services, and is shared among a plurality of members of emergency personnel. In addition, the timeline in the emergency stage is taken over to a hospital that is a transport destination, and is used as reference information for medical treatment by the medical staff in the hospital, such as doctors. Since a situation in the emergency stage can be checked through the timeline in the emergency stage, it is possible to perform appropriate medical treatment.

SUMMARY OF THE INVENTION

In order to perform appropriate medical treatment for a rescue requester, it is preferable that information regarding the rescue requester, such as an onset time, the condition of the rescue requester, or what kind of treatment has been performed for the rescue requester, can be understood in time series in the earliest possible stage immediately after the onset.

The medical assistance device disclosed in JP2015-32060A records information regarding the rescue requester in the emergency stage after the arrival of emergency personnel, who are healthcare workers, as a timeline. However, information regarding the rescue requester before the emergency stage cannot be recorded. Also before the emergency stage, for example, there are cases where initial rescue procedures, such as artificial respiration or automated external defibrillator (AED) treatment, are performed by rescuers around the rescue requester. In addition, rescuers around the rescue requester may have witnessed the situation of the rescue requester, such as the state of breathing or the condition of the rescue requester at the time of the onset of disease. In the medical field, such information regarding initial rescue procedures, which are performed in the initial stage before the emergency stage by emergency personnel, or the rescue requester including the condition of the rescue requester in the initial stage (hereinafter, referred to as initial rescue information) is very useful information for appropriately performing subsequent medical treatment. Therefore, measures to collect such information have been required. In the case of looking back on the initial rescue information later, it is very important to organize information so that in which order the initial rescue procedures and the like have occurred can be seen.

It is an object of the invention to provide an initial rescue information collection device, an operation method thereof, a non-transitory computer readable computer medium storing a program, and a system capable of collecting initial rescue information regarding a rescue requester before the emergency stage by healthcare workers and of allowing checking of the initial rescue information in a format in which the initial rescue information is organized in time series.

In order to achieve the aforementioned object, an initial rescue information collection device of the invention comprises a rescue request receiving unit, a rescue request notification transmission unit, an information receiving unit, and a timeline generation unit. The rescue request receiving unit receives a rescue request from a rescue requester who has sent the rescue request. The rescue request notification transmission unit selects users, who are present in a predetermined distance range from a current location of the rescue requester, among users registered in advance and transmits a rescue request notification to the selected users. The information receiving unit receives information from mobile terminals of the users who have received the rescue request notification, and receives initial rescue information after the rescue request notification. The initial rescue information is information regarding at least one of initial rescue procedures performed on the rescue requester in an initial stage before arrival of emergency personnel who are healthcare workers and a condition of the rescue requester in the initial stage. The timeline generation unit generates a timeline in which the initial rescue information is recorded in time series.

In addition, it is preferable to further comprise a timeline distribution unit that distributes the timeline to the mobile terminals of the plurality of users who have received the rescue request notification. In this case, since a plurality of users can view the timeline, the initial rescue information can be shared by a plurality of users present in the vicinity of the rescue requester. This makes work sharing between users or the like easy.

In addition, it is preferable to further comprise a mobile terminal current location acquisition unit that acquires current locations of mobile terminals of the users including a transmission source of the rescue request. It is preferable that the rescue request notification transmission unit selects the users, to whom the rescue request notification is to be transmitted, from the current locations of the mobile terminals. In this case, users in the vicinity of the rescue requester who has sent the rescue request can be selected as rescuers.

It is preferable to further comprise a timeline transmission unit that transmits the timeline, in which the initial rescue information is recorded, to a server that manages another timeline. It is preferable that medical procedures performed on the rescue requester by the healthcare workers after arrival of the emergency personnel are recorded in another timeline. In this case, after the arrival of emergency personnel, it is easy for the healthcare workers, who perform medical treatment for the rescue requester, to take over the timeline.

It is preferable to further comprise a timeline search unit and a timeline integration unit. The timeline search unit searches for a past timeline, in which past medical history of the rescue requester is recorded, based on an ID for identifying the rescue requester. The timeline integration unit integrates the timeline in which the initial rescue information is recorded with the past timeline. In this case, not only the initial rescue information of the rescue requester but also the past medical history can be taken over by healthcare workers. Therefore, it is possible to perform a medical examination quickly and accurately.

In a case where the past timeline is integrated with the timeline in which the initial rescue information is recorded, it is preferable that the timeline distribution unit distributes the timeline only to a user registered as a healthcare worker in advance. In this case, it is possible to limit the sharing of past timelines to healthcare workers.

It is preferable that the information receiving unit receives at least one of a still image, a motion picture, and a text as the initial rescue information. In this case, it is possible to generate the initial rescue information using one of the still image, the motion picture, and the text.

It is preferable that the information receiving unit receives information from a biological sensor that the rescue requester is wearing. In this case, the initial rescue information and the information of the biological sensor can be centrally managed in the timeline, which is convenient.

An operation method of an initial rescue information collection device of the invention comprises a rescue request receiving step, a rescue request notification transmission step, an information receiving step, and a timeline generation step. A non-transitory computer readable computer medium storing an initial rescue information collection program of the invention causes a computer to execute a rescue request receiving step, a rescue request notification transmission step, an information receiving step, and a timeline generation step. In the rescue request receiving step, a rescue request from a rescue requester who has sent the rescue request is received. In the rescue request notification transmission step, users present in a predetermined distance range from a current location of the rescue requester, among users registered in advance, are selected, and a rescue request notification is transmitted to the selected users. In the information receiving step, initial rescue information is received from mobile terminals of the users who have received the rescue request notification. The initial rescue information is information regarding at least one of initial rescue procedures on the rescue requester, which are performed before arrival of emergency personnel who are healthcare workers, and a condition of the rescue requester after the rescue request notification. In the timeline generation step, a timeline in which the initial rescue information is recorded in time series is generated.

An initial rescue information collection system of the invention comprises a mobile terminal and an initial rescue information collection device that is able to communicate with the mobile terminal through a network. The initial rescue information collection device comprises a rescue request receiving unit, a rescue request notification transmission unit, an information receiving unit, and a timeline generation unit. The rescue request receiving unit receives a rescue request from a rescue requester who has sent the rescue request. The rescue request notification transmission unit selects users, who are present in a predetermined distance range from a current location of the rescue requester, among users registered in advance and transmits a rescue request notification to the selected users. The information receiving unit receives information from mobile terminals of the users who have received the rescue request notification. The information receiving unit receives initial rescue information regarding at least one of initial rescue procedures, which are performed on the rescue requester before arrival of emergency personnel who are healthcare workers, and a condition of the rescue requester after the rescue request notification. The timeline generation unit generates a timeline in which the initial rescue information is recorded in time series.

According to the invention, there are provided an initial rescue information collection device, an operation method thereof, a non-transitory computer readable computer medium storing a program, and a system capable of collecting initial rescue information regarding a rescue requester before the emergency stage by healthcare workers and of allowing checking of the initial rescue information in a format in which the initial rescue information is recorded in time series.

BRIEF DESCRIPTION OF THE DRAWINGS

FIG. 14 is an explanatory diagram showing an integrated timeline of another embodiment using information from a biological sensor.

DESCRIPTION OF THE PREFERRED EMBODIMENTS

First Embodiment

Figure 1:
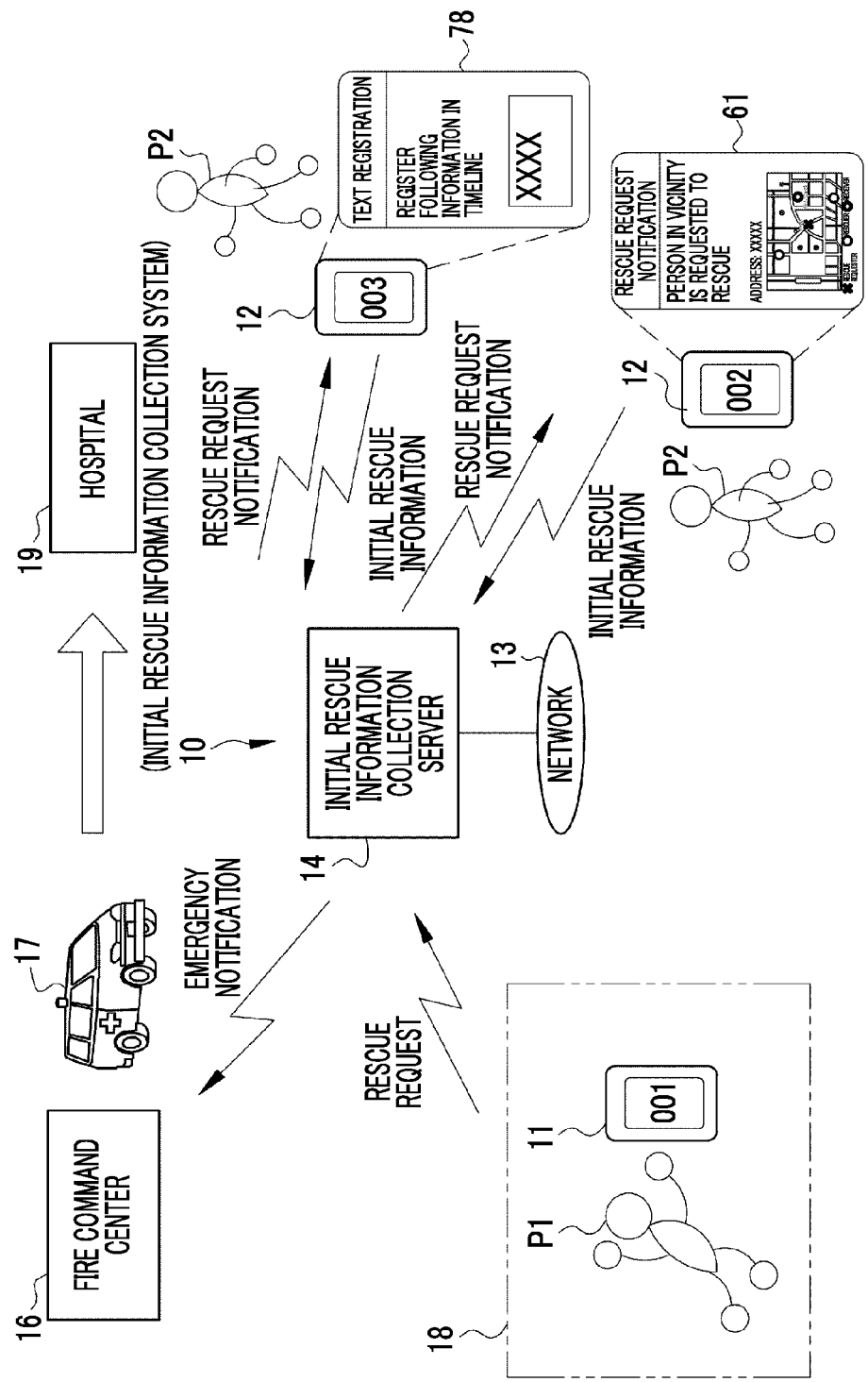
FIG. 1 is an explanatory diagram of an initial rescue information collection system configured to include a mobile terminal and an initial rescue information collection server.

As shown in FIG. 1, an initial rescue information collection system 10 is formed by an initial rescue information collection server (initial rescue information collection device) 14 that can communicate with mobile terminals 11 and 12 through a network 13. The initial rescue information collection server (hereinafter, simply referred to as an information collection server) 14 provides application services for initial rescue information collection to users, who are registered in advance, through the network 13.

The users registered in advance are users carrying the mobile terminals 11 and 12, and are users who have completed registration for the use of application services provided by the information collection server 14. The initial rescue information is information regarding a rescue requester P1 including initial rescue procedures on the rescue requester P1, which are performed by a rescuer P2 who is a user located close to a field of emergency 18 where the rescue requester P1 is present, the state of the rescue requester P1, the situation of the field of emergency 18, and the like, and refers to information in the initial stage before the emergency stage by emergency personnel who are healthcare workers. The information collection server 14 provides application services for collecting initial rescue information uploaded from the mobile terminal 12 of the rescuer P2 in the initial stage before emergency personnel arrive in the field of emergency 18 where the rescue requester P1 is present.

The information collection server 14 receives a rescue request from the rescue requester P1, and provides application services for transmitting a rescue request notification to a user who is the rescuer P2 close to the field of emergency 18 where the rescue requester P1 is present.

Specifically, in a case where an emergency occurs in a user, if the user transmits a rescue request to the information collection server 14, the user becomes the rescue requester P1. The rescue request is transmitted from the mobile terminal 11 of the rescue requester P1. When the rescue request is received, the information collection server 14 selects another user close to the current location of the rescue requester P1, as the rescuer P2, from users other than the rescue requester P1, and transmits a rescue request notification. Here, the emergency refers to a case where a condition change or injury has occurred in the user due to sudden attack of a chronic disease, accident, or the like. The rescuer P2 refers to a person who has received the rescue request from the rescue requester P1.

The user has a potential to become the rescue requester P1 or the rescuer P2. There is also a case where the owner of the mobile terminal 11 is the rescuer P2 or a case where the owner of the mobile terminal 12 is the rescue requester P1. In this example, for convenience of explanation, an example will be described in which a user holding the mobile terminal 11 is the rescue requester P1 and a user holding the mobile terminal 12 is the rescuer P2.

In addition, the information collection server 14 provides services for transmitting an emergency notification to a fire command center 16 in a case where the rescue request from the rescue requester P1 is received. In the fire command center 16, emergency personnel who are healthcare workers are on standby. Accordingly, the fire command center 16 organizes emergency services 17 including a plurality of members of emergency personnel based on the emergency notification, and dispatches the emergency services 17 to the field of emergency 18. The emergency services 17 convey the rescue requester P1 to a hospital 19 after arriving in the field of emergency 18. Thus, in the emergency stage after the arrival of the emergency services 17, rescue or treatment is performed on the rescue requester P1 by the emergency services 17. In the information collection server 14, information regarding the rescue requester P1 in the initial stage before such an emergency stage is collected. Then, the collected information is taken over to the emergency services 17.

Figure 2:
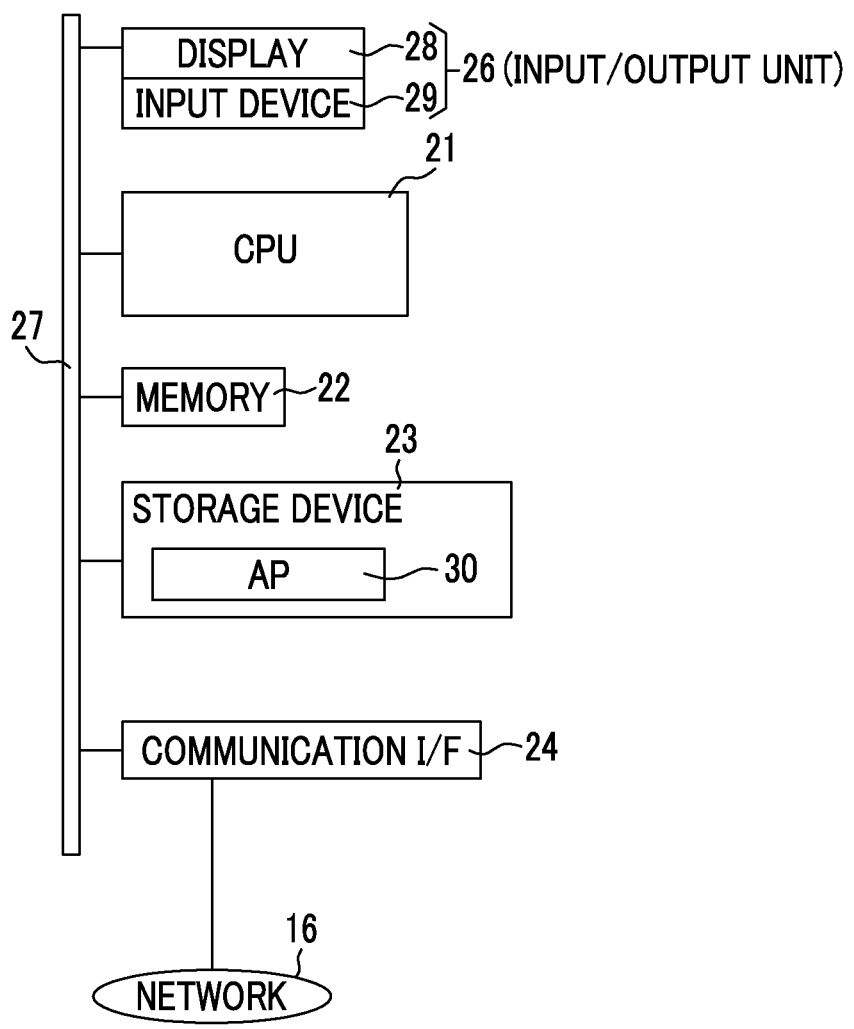
FIG. 2 is a block diagram showing the schematic configuration of a computer.

The mobile terminals 11 and 12 are small computers, for example. The schematic configuration of a general computer is shown in FIG. 2, and the basic configuration of each of the mobile terminals 11 and 12 is the same as the schematic configuration of a general computer. As shown in FIG. 2, a computer includes a central processing unit (CPU) 21, a memory 22, a storage device 23, a communication I/F 24, and an input/output unit 26. These are connected to each other through a data bus 27. The input/output unit 26 is configured to include a display 28 and an input device 29, such as an operation key. The display 28 is, for example, a touch panel display. In this case, the display 28 also functions as the input device 29.

The storage device 23 is, for example, a hard disk drive (HDD) or a solid state drive (SSD), and a control program or an application program (hereinafter, referred to as an AP) 30 is stored in the storage device 23. In the case of the mobile terminals 11 and 12, the storage device 23 is, for example, an SSD.

The memory 22 is a work memory required when the CPU 21 executes processing, and is a random access memory (RAM). The CPU 21 performs overall control of each unit of the computer by loading a control program stored in the storage device 23 to the memory 22 and executing the processing according to the program.

The communication I/F 24 is a network interface for transmission control through the network 13. In the case of the mobile terminals 11 and 12, the communication I/F 24 is, for example, a wireless communications module, and the network 13 is, for example, a mobile communication network or a wireless LAN.

Figure 3:
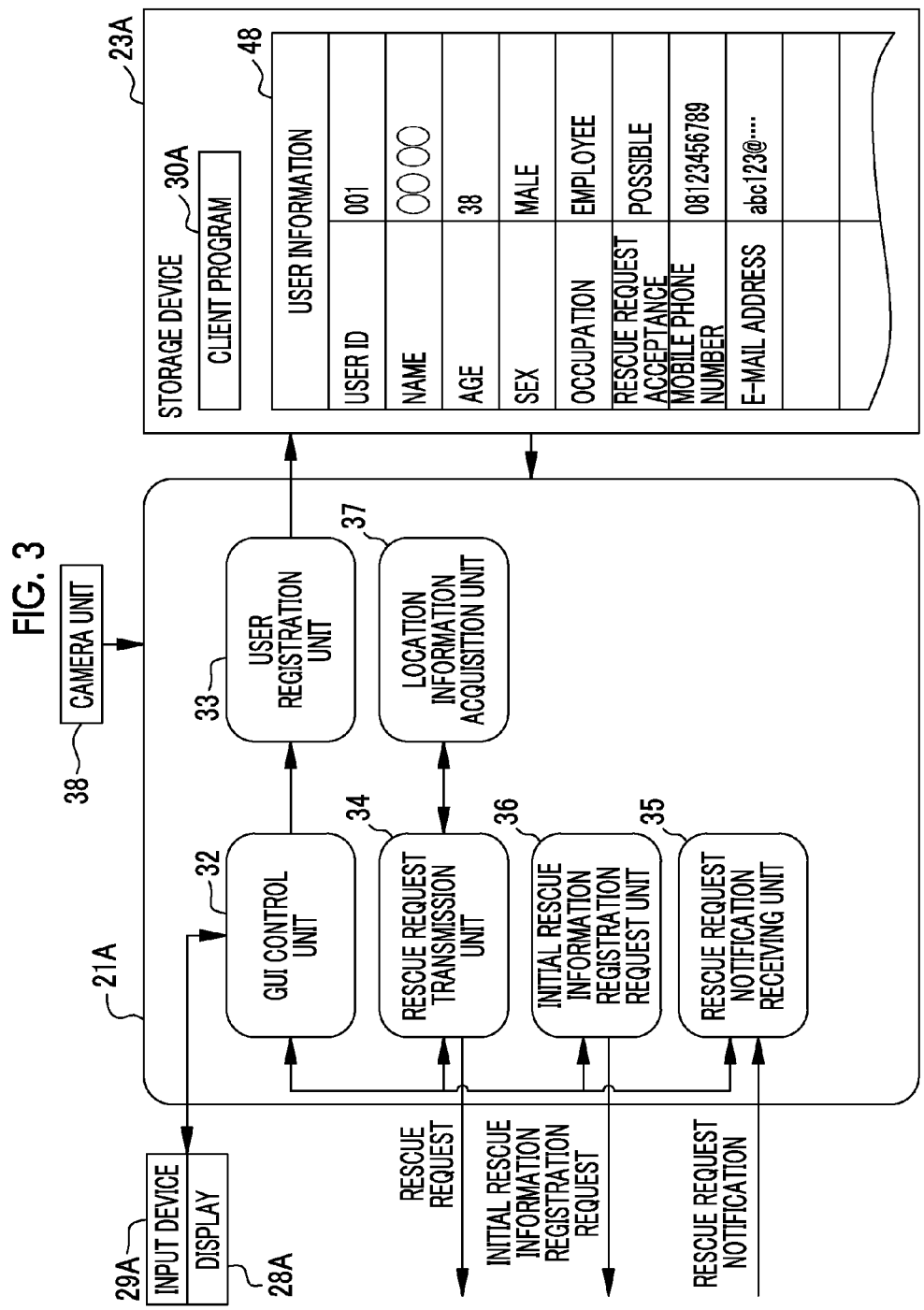
FIG. 3 is a functional block diagram of a mobile terminal.

As shown in FIG. 3, in the mobile terminals 11 and 12, a camera unit 38 for taking photos or motion pictures or a microphone (not shown) to record the voice for motion picture capturing is also provided in addition to the general configuration of the computer shown in FIG. 2.

In the mobile terminals 11 and 12, a client program 30A for initial rescue information collection is installed as the AP 30 for using the application services of the information collection server 14. The client program 30A realizes a function of transmitting a rescue request to the information collection server 14, a function of receiving a rescue request notification from the information collection server 14, a function of transmitting the initial rescue information of the rescue requester P1 to the information collection server 14, and the like in the mobile terminal 11 or the mobile terminal 12.

The function of transmitting the rescue request is a function that is used in the mobile terminal 11 by the rescue requester P1, and the function of receiving the rescue request notification and the function of transmitting the initial rescue information are functions that are used in the mobile terminal 12 by the rescuer P2. As described above, distinction between the mobile terminal 11 of the rescue requester P1 and the mobile terminal 12 of the rescuer P2 is intended for convenience, and both the mobile terminals 11 and 12 in which the client program 30A is installed have these functions. Therefore, the respective functions realized by the client program 30A will be collectively described below without distinction between the mobile terminals 11 and 12.

Here, for the configuration of a computer used as the mobile terminals 11 and 12, a letter "A" is given after a reference numeral, for example, as a CPU 21A, for convenience of explanation, so that the configuration of the computer used as the mobile terminals 11 and 12 is distinguished from the configuration (refer to FIG. 7) of a computer of the information collection server 14 to be described later.

The client program 30A can be downloaded from a company that operates the information collection server 14, for example. When the downloaded client program 30A is executed, the CPU 21A of each of the mobile terminals 11 and 12 functions as a graphical user interface (GUI) control unit 32, a user registration unit 33, a rescue request transmission unit 34, a rescue request notification receiving unit 35, an initial rescue information registration request unit 36, and a location information acquisition unit 37.

The GUI control unit 32 displays an operation screen on the display 28A, and receives various operation instructions through the operation screen. The user registration unit 33 registers user information 48 input through the GUI control unit 32. The user information 48 is stored in the storage device 23A and is then transmitted to the information collection server 14, so that the user registration of the user information 48 is performed in the information collection server 14. At this time, a user ID is issued from the information collection server 14. The issued user ID is recorded in the user information 48. When communication is performed between the mobile terminals 11 and 12 of the registered users and the information collection server 14, the user ID is transmitted to the information collection server 14 from each of the mobile terminals 11 and 12. Based on the user ID, the information collection server 14 identifies a user.

Figure 4:
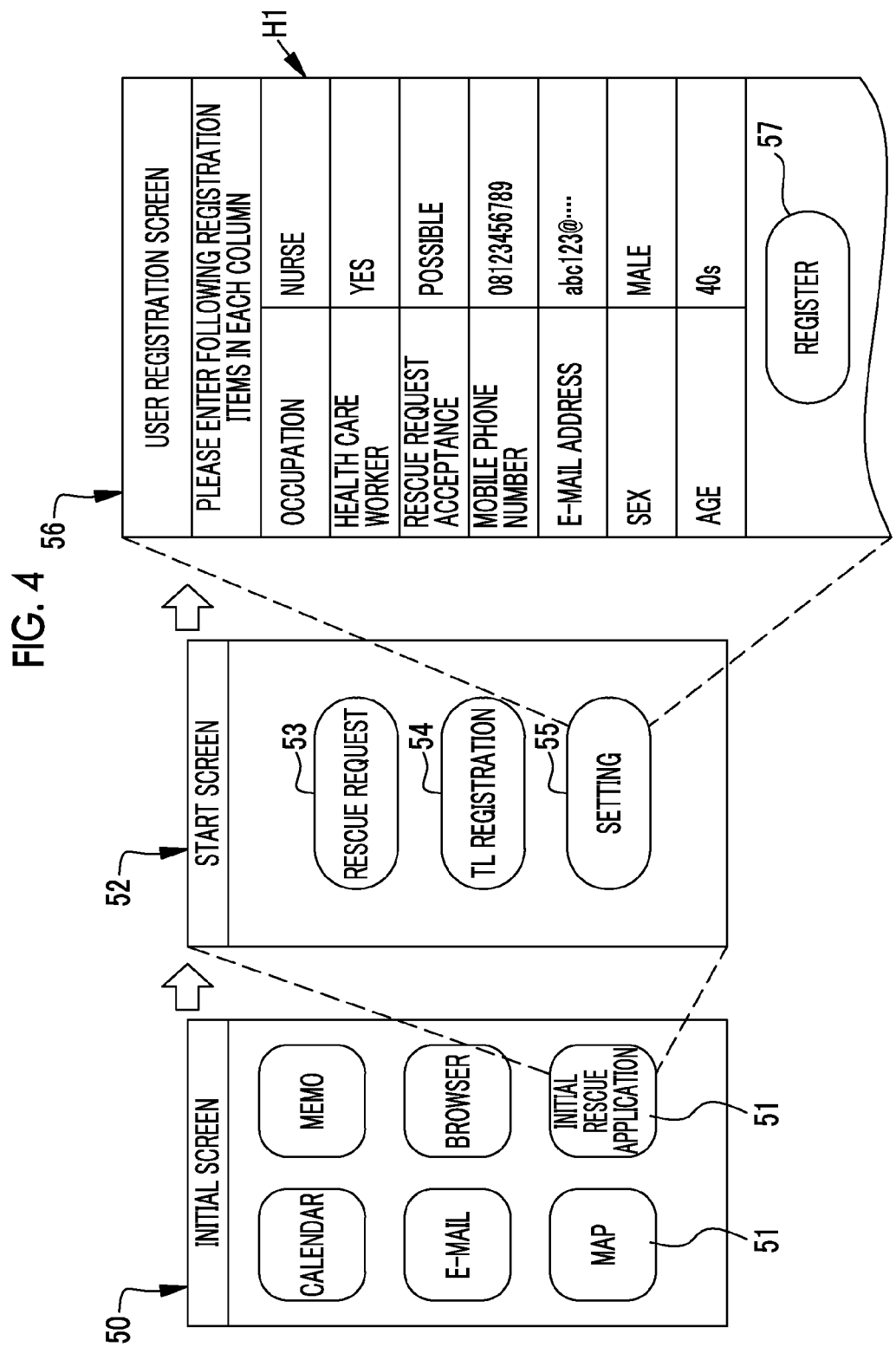
FIG. 4 is an explanatory diagram showing the transition of an operation screen of a mobile terminal at the time of user registration.

The GUI control unit 32 receives an input of operation screen display control through the GUI or an input of an operation instruction through the operation screen. As shown in FIG. 4, the operation screen includes, for example, an initial screen 50, a start screen 52, and a user registration screen 56. Icons 51 of various applications, such as e-mail, a browser, a calendar, and a map, are displayed on the initial screen 50. In a case where the client program 30A is installed, the icon 51 of "initial rescue application" for starting the client program 30A is displayed as one of the icons 51. When the icon 51 is operated, the initial screen 50 transitions to the start screen 52 of the client program 30A.

A rescue request button 53, a timeline (TL) registration button 54, and a setting button 55 are provided on the start screen 52. When the setting button 55 is operated on the start screen 52, the user registration screen 56 is displayed. On the user registration screen 56, a message prompting the input of user information is displayed, and an input field H1 for inputting user information or a registration button 57 for registering the input user information in the information collection server 14 is provided.

At the time of input to the input field H1, a character input pad (not shown) for characters or alphanumeric characters, such as a ten key, is displayed in a part of the screen, so that it is possible to input the user information 48. Items of the user information 48 to be registered include name, sex, age, mobile phone number, e-mail address, occupation, information regarding rescue request acceptance, and the like, and the input field H1 is divided into these items. The information regarding rescue request acceptance is information indicating the intention of a user regarding whether or not the user can act as the rescuer P2 in a case where there is a rescue request. Users for whom the information regarding rescue request acceptance is "impossible" are excluded from rescue request notification targets.

Referring back to FIG. 3, the user registration unit 33 receives the user information 48 input through the user registration screen 56 (refer to FIG. 4), and stores the user information 48 in the storage device 23A. When the registration button 57 (refer to FIG. 4) is operated, the user registration unit 33 reads the user information 48 in the storage device 23A, and transmits a registration request of the user information 48 to the information collection server 14. In this manner, the user information 48 from the mobile terminals 11 and 12 is registered in the information collection server 14.

In the start screen 52 (refer to FIG. 4), the rescue request button 53 is an operation button for instructing the transmission of a rescue request. When the rescue request button 53 is operated, the operation instruction is input to the rescue request transmission unit 34 through the GUI control unit 32.

In response to the operation of the rescue request button 53, the rescue request transmission unit 34 performs processing for transmitting the rescue request. The rescue request notification receiving unit 35 receives the rescue request notification from the information collection server 14. The GUI control unit 32 displays a rescue request notification screen 61 (refer to FIG. 8) on the display 28A in a case where the rescue request notification is received.

Referring back to FIG. 3, the initial rescue information registration request unit 36 transmits the initial rescue information, which is input through the GUI control unit 32, to the information collection server 14. Initial rescue information registration is performed through the operation screen shown in FIG. 5.

Figure 5:
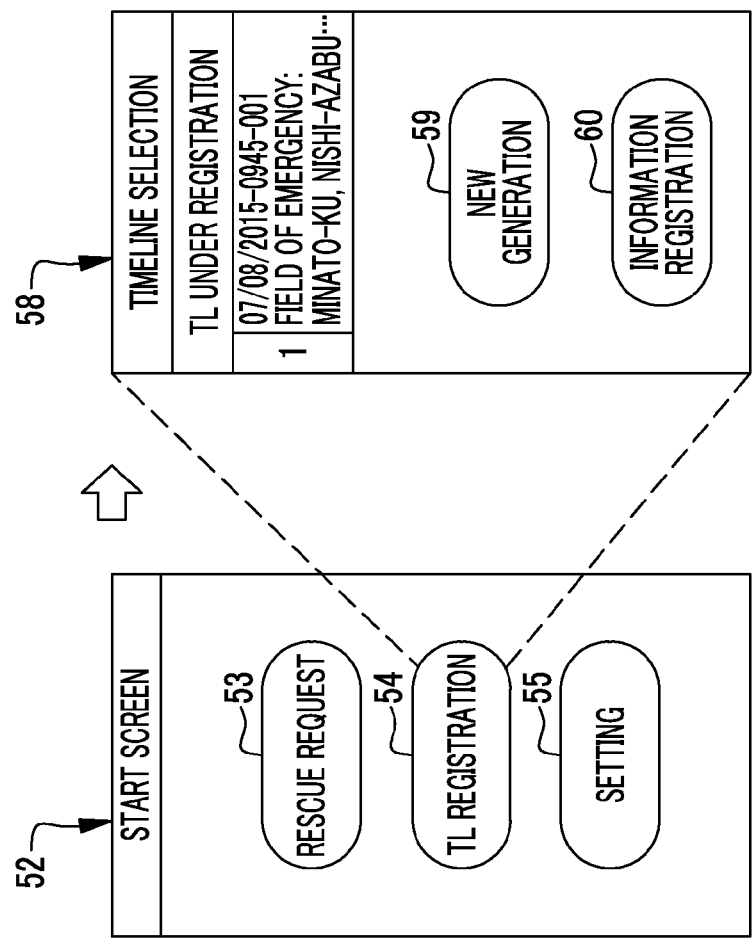
FIG. 5 is an explanatory diagram showing an example of timeline selection.

As shown in FIG. 5, a TL registration button 54 is provided on the start screen 52. The timeline refers to information in a format, in which collected initial rescue information is recorded in time series, in the information collection server 14, as will be described later (refer to FIG. 9). A timeline is generated in the information collection server 14. When the initial rescue information is received from the mobile terminal 12, the information collection server 14 registers the initial rescue information in the timeline in the received order. By such registration of initial rescue information, a timeline in which the initial rescue information is recorded in time series is generated.

The TL registration button 54 is an operation button for requesting the registration of initial rescue information in the timeline. When the TL registration button 54 is operated, transition to a timeline selection screen 58 occurs. The timeline selection screen 58 is a screen to select a timeline in which the initial rescue information is to be registered.

The timeline that is being registered in the information collection server 14 is displayed on the timeline selection screen 58. The mobile terminal 12 accesses the information collection server 14 to receive the timeline that is being registered in the information collection server 14, and displays the received timeline on the timeline selection screen 58. In this example, one timeline under registration is displayed. In a case where there is a plurality of timelines that are being registered in the information collection server 14, the plurality of timelines are displayed. In a case where there is no timeline under registration, no timeline is displayed.

On the timeline selection screen 58, a timeline ID is displayed in the displayed timeline. For example, the timeline ID is a numeric string ("07/08/2015-0948-001") obtained by adding the user ID (in this example, "001") to the generation date and time (in this example, "09:48, July 8, 2015") that is newly generated. In addition to the timeline ID, the address ("Minato-ku, Nishi-Azabu, . . . ") of the field of emergency 18 of the rescue requester P1 who has transmitted the rescue request is displayed.

In a case where a plurality of timelines are displayed, the rescuer P2 who registers the initial rescue information matches the display of the timeline ID or the address with the current time or the current location of the rescue requester P1, and selects the timeline at the registration destination. At a time when the rescuer P2 registers the initial rescue information, the rescuer P2 has already arrived in the field of emergency 18 where the rescue requester P1 is present. The rescuer P2 selects a timeline close to the current time or the address of the field of emergency 18 where the rescuer P2 is present.

A new generation button 59 and an information registration button 60 are provided on the timeline selection screen 58. The new generation button 59 is an operation button for transmitting a request to newly generate a timeline to the information collection server 14.

Even in a case where there is no timeline under registration or a case where there is a timeline under registration, a timeline is newly generated in a case where there is no timeline corresponding to the field of emergency 18 where the rescuer P2 is present. When a new generation request is transmitted, processing for newly generating the timeline is executed by the information collection server 14, and the newly generated timeline is additionally displayed on the timeline selection screen 58. A timeline ID issued based on the generation date and time is given to the newly generated timeline. In addition, the address of the field of emergency 18 is given based on the current location of the mobile terminal 12 that has transmitted the new generation request. The timeline ID and the address given in this manner are displayed in the new timeline that is additionally displayed on the timeline selection screen 58.

The timeline under registration is shared by a plurality of rescuers P2 through the timeline selection screen 58. Each rescuer P2 can select the timeline in his or her own mobile terminal 12, and register initial rescue information.

Figure 6:
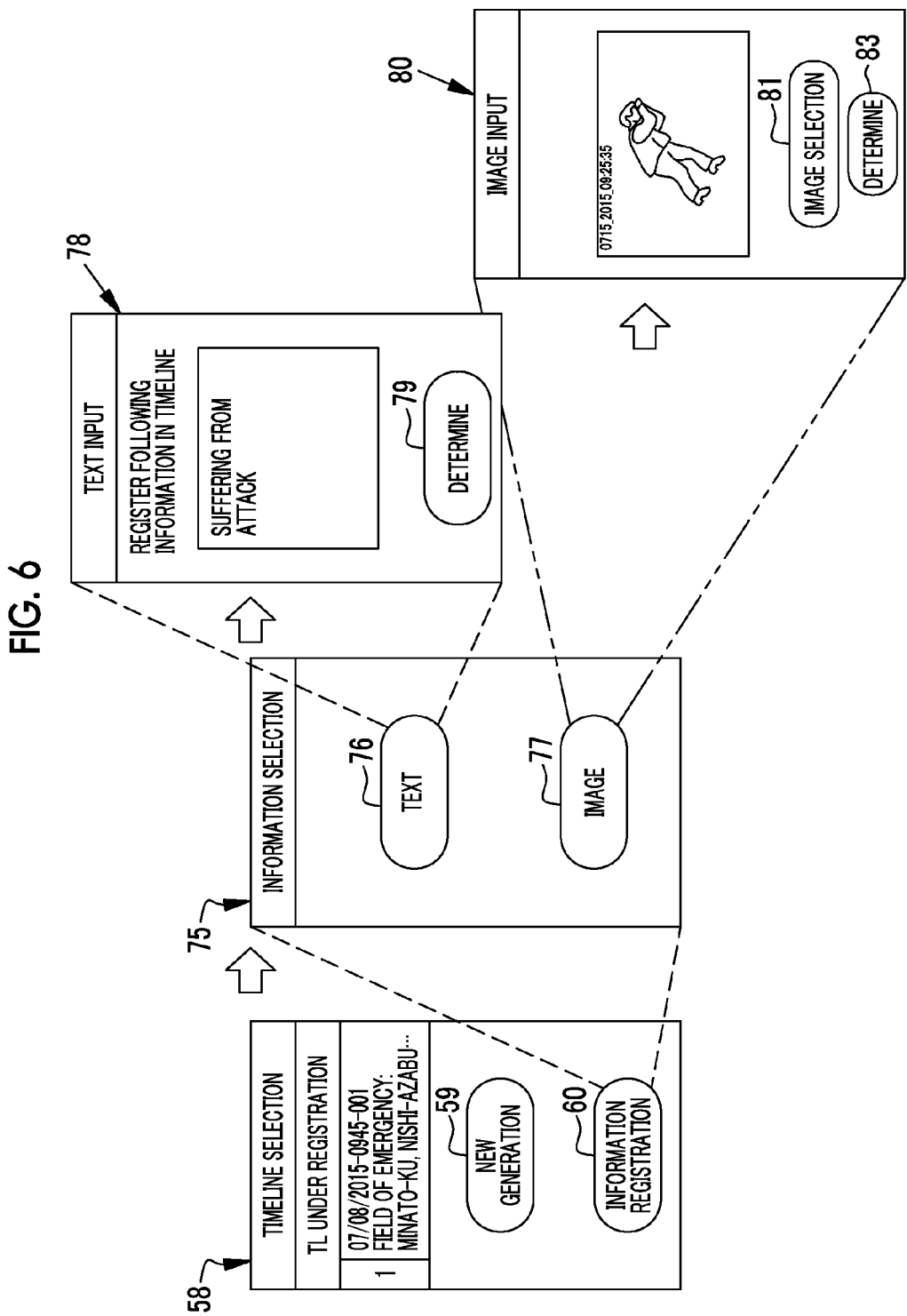
FIG. 6 is an explanatory diagram showing the transition of an operation screen of a mobile terminal at the time of timeline registration.

The information registration button 60 is an operation button for inputting the initial rescue information registered in the timeline. As shown in FIG. 6, when the information registration button 60 is operated in a state in which the timeline is selected on the timeline selection screen 58, transition to an information selection screen 75 occurs. The information selection screen 75 is a screen to select the type of information to be registered. In this example, a text and an image can be selected as the type of information. Therefore, a selection button 76 for selecting a text and a selection button 77 for selecting an image are provided.

When the selection button 76 is operated, a text input screen 78 is displayed. A text input field is provided on the text input screen 78, so that the initial rescue information can be input in text through a character input pad (not shown) displayed on the screen. In this example, a text showing the state of the rescue requester P1, such as "suffering from the attack", is input as the initial rescue information. When a determination button 79 is operated after inputting the text, a request to register the input text is transmitted.

The initial rescue information registration request unit 36 generates a registration request by adding a header including the transmission time or the user ID of the mobile terminal 12, which is a transmission source, to the text to be registered, and transmits the generated registration request to the information collection server 14.

When the selection button 77 is operated, an image input screen 80 is displayed. An image selection button 81 is provided on the image input screen 80. When the image selection button 81 is operated, an image selection screen (not shown) to select an image to be registered is displayed, so that it is possible to select an image on the image selection screen. In the image, the appearance of the rescue requester P1 or the situation of the field of emergency 18 is captured by the camera unit 38 of the mobile terminal 12. The image may be a still image or a motion picture.

When an image is selected on the image selection screen, the selected image is displayed on the image input screen 80. When a determination button 83 is operated in this state, an initial rescue information registration request including the selected image is generated by the initial rescue information registration request unit 36 in the same manner as in the case of a text, and is transmitted to the information collection server 14.

In addition, it is also possible to display a timeline selected in the mobile terminal 12 by giving a reading instruction through an operation button (not shown) on the timeline selection screen 58.

The location information acquisition unit 37 acquires the location information indicating the current locations of the mobile terminals 11 and 12 using a GPS system, a base station method, or the like. The location information acquisition unit 37 transmits the location information of the mobile terminals 11 and 12 periodically to the information collection server 14. Transmission and reception of information, such as a rescue request, a rescue request notification, location information, the user information 48, and initial rescue information, between the location information acquisition unit 37 and the information collection server 14 are performed through the communication I/F 24A and the network 13.

Figure 7:
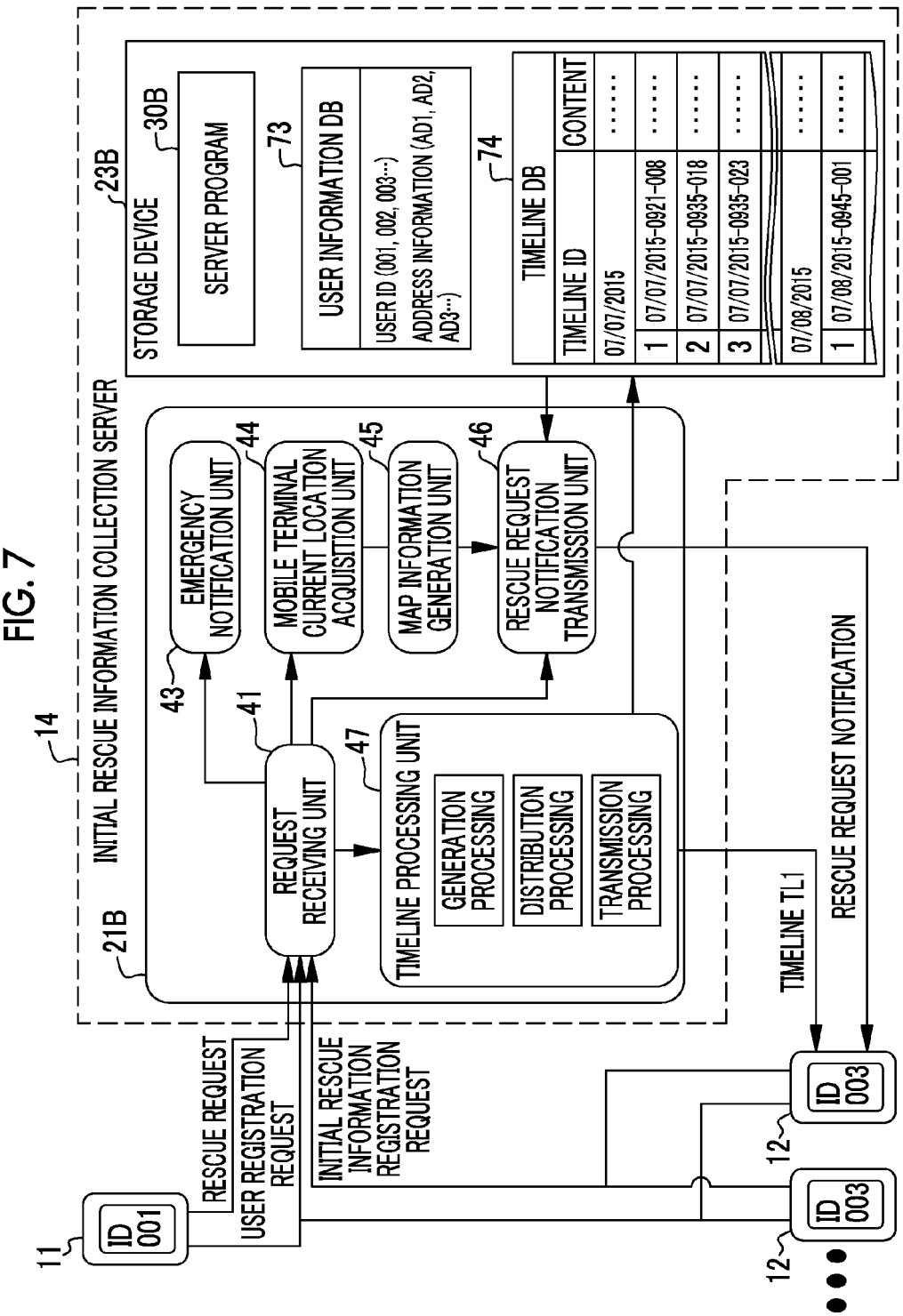
FIG. 7 is a functional block diagram of an initial rescue information collection server.

The information collection server 14 is also a computer, and the basic configuration is as shown in FIG. 2 similarly to the mobile terminals 11 and 12. As shown in FIG. 7, a server program 30B for initial rescue information collection is stored in the storage device 23B of the information collection server 14. The server program 30B corresponds to an initial rescue information collection program defined by the appended claims.

When the server program 30B is executed, the CPU 21B of the information collection server 14 functions as a request receiving unit 41, an emergency notification unit 43, a mobile terminal current location acquisition unit 44, a map information generation unit 45, a rescue request notification transmission unit 46, and a timeline processing unit 47. Here, for convenience of explanation, for the configuration of the CPU or the like of the information collection server 14, a letter "B" is given after a reference numeral, so that the configuration of the CPU or the like of the information collection server 14 is distinguished from the configuration of the CPU or the like of the mobile terminals 11 and 12 ("A" is given after a reference numeral).

The request receiving unit 41 functions as a rescue request receiving unit, and receives a user registration request, a rescue request, and an initial rescue information registration request from the mobile terminals 11 and 12 and sends an instruction corresponding to the received request to each unit.

In addition, the request receiving unit 41 registers the user information 48 (refer to FIG. 3), which is included in the user registration request from the mobile terminals 11 and 12, in a user information DB 73. The user information 48 is stored in the storage device 23B. As described above, at the time of user registration, a user ID for identifying each user is issued, and the mobile terminals 11 and 12 that have transmitted the user registration request are notified of the issued user ID.

When a rescue request is received from the mobile terminal 11, the emergency notification unit 43 transmits an emergency notification to the fire command center 16. The name, mobile phone number, sex, and age of the rescue requester P1 specified from the user ID, the current location of the rescue requester P1, or an emergency rescue service request is included in the emergency notification.

The mobile terminal current location acquisition unit 44 acquires location information that is periodically transmitted from the mobile terminals 11 and 12. The mobile terminal current location acquisition unit 44 stores the acquired location information in a current location table (not shown) for each user ID. The current location table is stored in the storage device 23B. In this example, the acquisition interval of the location information from each of the mobile terminals 11 and 12 is 30 seconds, for example. In addition to the latest location information, location data up to a certain time, for example, location data before five minutes may be recorded in the current location table. In this case, it is possible to see the movement direction of each mobile terminal 12 based on the current location and the position before five minutes.

Figure 8:
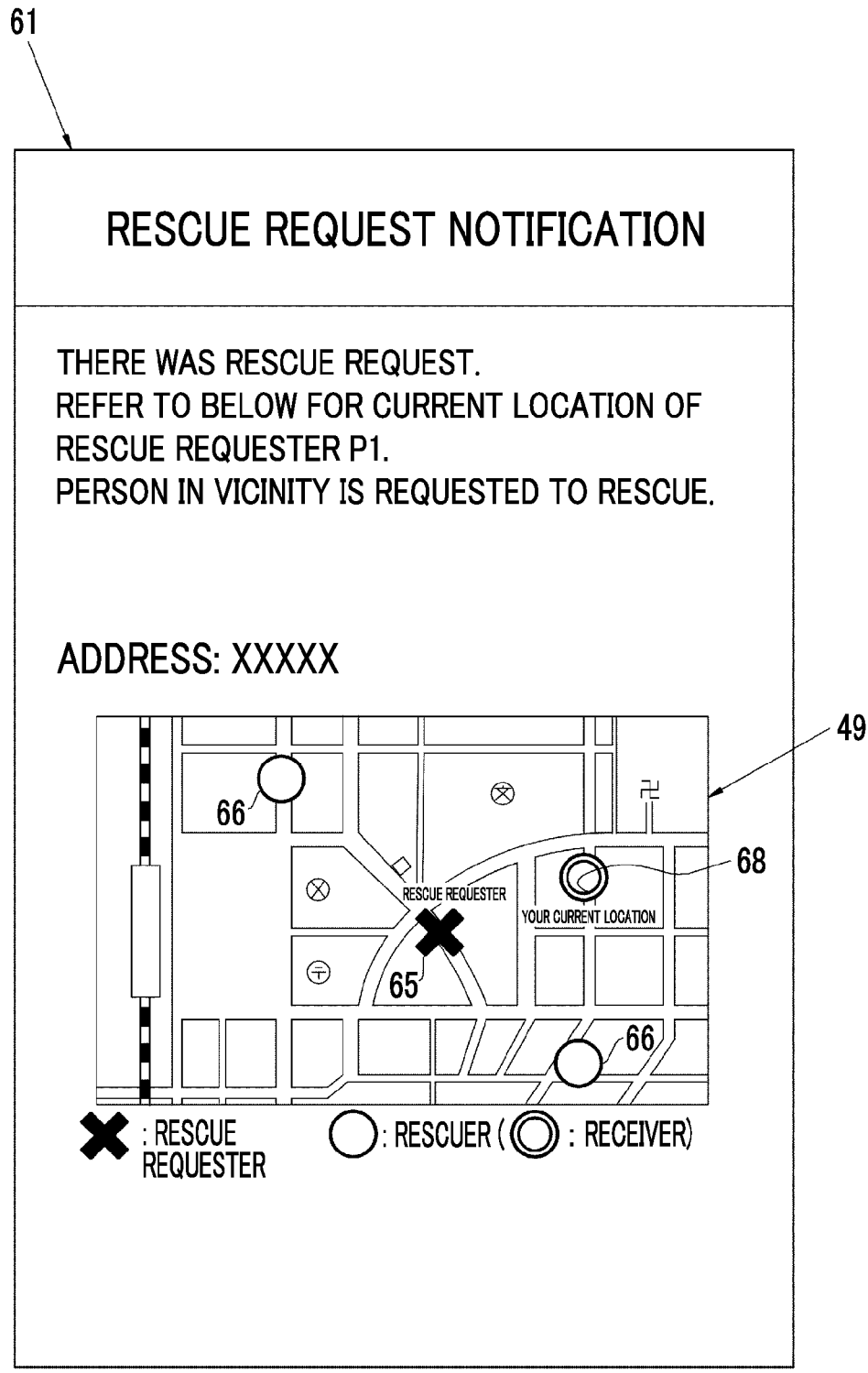
FIG. 8 is an explanatory diagram showing an example of a rescue request notification screen.

In a case where the request receiving unit 41 receives a rescue request, the map information generation unit 45 generates map information 49 to be displayed on the rescue request notification screen 61 shown in FIG. 8, in which the current locations of the rescue requester P1 and the rescuer P2 are mapped.

As shown in FIG. 8, in the map information 49, for example, a map of the area of a predetermined range around the current location of the rescue requester P1 is displayed. On the map, marks indicating the current locations of the rescue requester P1 and the rescuer P2 are displayed.

The current location of the rescue requester P1 is displayed with a rescue requester mark 65, and the rescuer P2 is displayed with a rescuer mark 66. In this example, an "X" mark is assigned as a form of the rescue requester mark 65, and an "O" mark is assigned as a form of the rescuer mark 66.

In addition, a principal mark 68 indicating a recipient himself or herself who has received a rescue request notification including the map information 49 in the mobile terminal 12 is displayed in the map information 49. Since the recipient himself or herself is the rescuer P2, the principal mark 68 is a form of a double circle "⊚" obtained by adding a slightly smaller "o" mark to the "O" mark of the rescuer mark 66. Therefore, distinction from the other rescuers P2 is possible.

In the map information 49, a note that is a description regarding what each mark of the rescue requester mark 65 ("X"), the rescuer mark 66 ("O"), and the principal mark 68 ("double circle ⊚") indicates is displayed. Also on the map, as a mark description, a character display of "rescue requester" is inserted in the vicinity of the rescue requester mark 65, and a character display of "your current location" is inserted in the vicinity of the principal mark 68. Through such a note or character display, it is possible to see what each mark on the map indicates.

The map information generation unit 45 generates the map information 49 as follows, for example. First, in a case where the request receiving unit 41 receives a rescue request, the map information generation unit 45 reads the current location of the rescue requester P1 from the current location table. Then, the map information generation unit 45 selects the rescuer P2 from users registered in advance based on the current location of the rescue requester P1. A user present in the vicinity of the rescue requester P1 who has sent a rescue request or a user present in a predetermined distance range from the current location of the rescue requester P1 is selected as the rescuer P2.

Specifically, the map information generation unit 45 sets a predetermined distance range from the current location of the rescue requester P1 as a search area. As the predetermined distance range, for example, a range within a radius of 400 m (approximately within a 5-minute walk) from the current location of the rescue requester P1 is set. Then, users whose current locations are within the search area are searched for with reference to the current locations of users recorded in the current location table. In addition, with reference to the user information DB 73, users for whom the information regarding rescue request acceptance is "impossible" are excluded from the users in the search area. A user extracted as described above is selected as the rescuer P2.

After selecting the rescuer P2, the map information generation unit 45 acquires the data of a map within the area of a predetermined range around the current location of the rescue requester P1 from a map server (not shown). Position information, such as global positioning system (GPS) information, is associated with the data of the map for each point on the map. The map information generation unit 45 maps the current locations of the rescue requester P1 and the rescuer P2 using the rescue requester mark 65 and the rescuer mark 66.

The rescue request notification transmission unit 46 distributes the map information 49 generated by the map information generation unit 45 to the mobile terminal 12 of the rescuer P2 in a state in which the map information 49 is included in the rescue request notification. When the rescue request notification is received, the mobile terminal 12 displays the rescue request notification screen 61 shown in FIG. 8.

In addition, in a case where the map information 49 needs to be updated, for example, in a case where the current location of the rescue requester P1 has changed, the rescue request notification transmission unit 46 distributes update information to the mobile terminal 12 of the rescuer P2 at any time. The mobile terminal 12 updates the map information 49 being displayed on the display 28A based on the update information.

The timeline processing unit 47 executes timeline generation processing, timeline distribution processing, and timeline transmission processing. The timeline processing unit 47 functions as an information receiving unit that receives an initial rescue information registration request through the request receiving unit 41. A timeline DB 74 is stored in the storage device 23B, and the generated timeline is recorded in the timeline DB 74.

Figure 9:
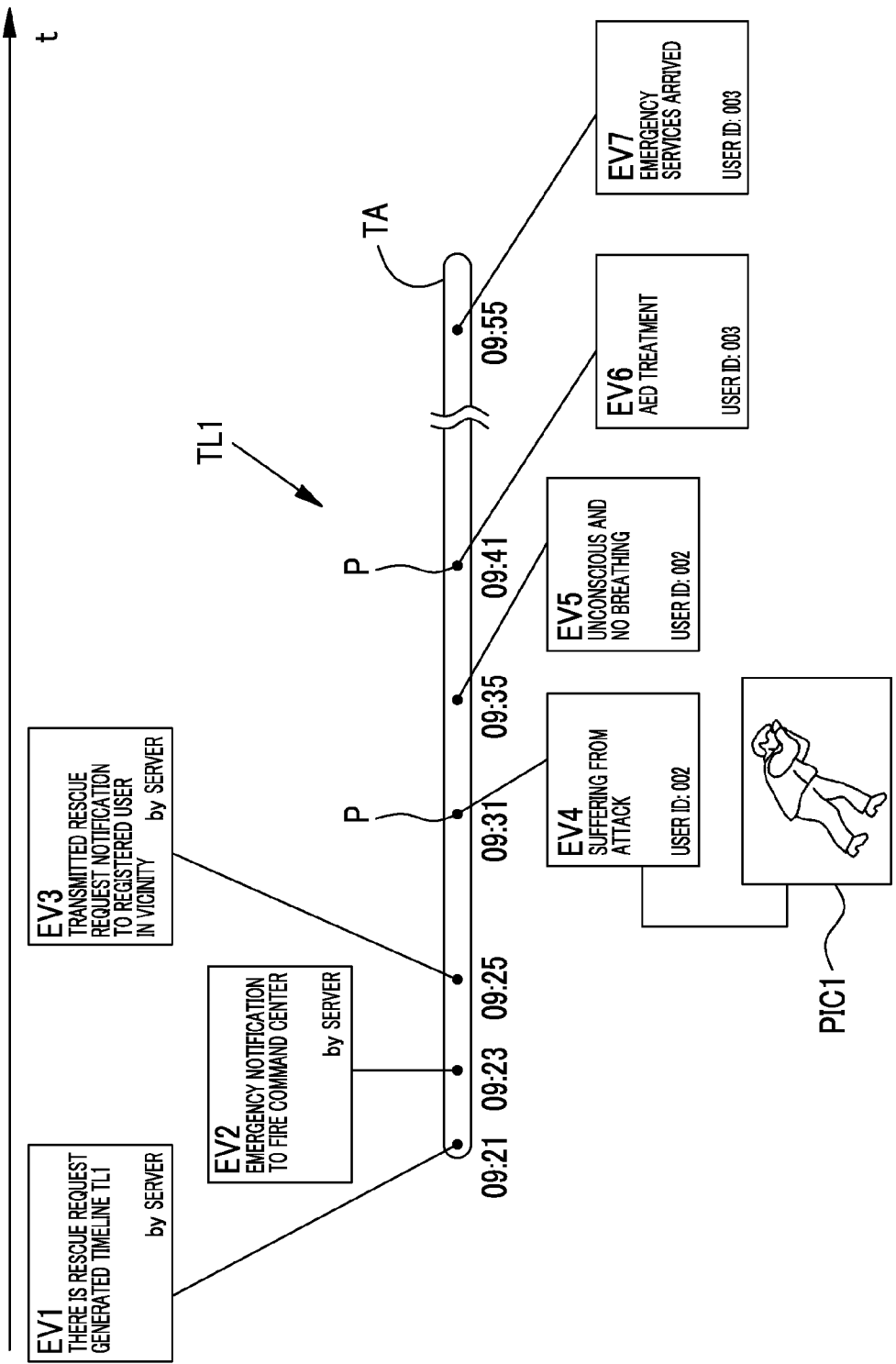
FIG. 9 is an explanatory diagram showing an example of the initial rescue information timeline.

As described above, the timeline refers to information in a format in which collected initial rescue information is recorded in time series. Specifically, the timeline processing unit 47 generates a timeline TL1 as shown in FIG. 9. In the timeline generation processing, the timeline processing unit 47 generates the timeline TL1 by recording an event EV (EV1, EV2, EV3, ... ) including the collected initial rescue information in time series along a time axis TA.

In each event EV, on the time axis TA, a registration time registered in the timeline TL1 is recorded. The registration time is displayed as "09:21" in the vicinity of a generation time of each event EV shown on the time axis TA. Therefore, it is possible to check the generation time of each event.

In addition to the initial rescue information collected from the mobile terminal 12, an event registered by the information collection server 14 is included in each event EV. For example, a comment showing that the timeline TL1 has been generated based on the rescue request is recorded in the event EV1. A comment showing that the information collection server 14 has transmitted an emergency notification is recorded in the event EV2, and a comment showing that a rescue request notification has been transmitted to a registered user in the vicinity of the rescue requester P1 is recorded in the event EV3.

Events EV4 to EV7 are initial rescue information collected from the rescuer P2 who is a registered user. Specifically, the events EV4 to EV7 are initial rescue information registered by the rescuer P2 through the mobile terminal 12. Comments showing the condition of the rescue requester P1, such as the state of breathing or the condition of the rescue requester P1 at the time of the onset of disease, are recorded in the events EV4 and EV5. For example, "suffering from the attack" or "unconscious and no breathing" is recorded in the events EV4 and EV5. In addition to the comment, an image PIC1 obtained by capturing the appearance of the rescue requester P1 is added to the event EV4. A comment showing the content of the initial rescue procedures that have been performed, such as "AED treatment" is recorded in the event EV6. A comment showing that the emergency services 17 have arrived is recorded in the event EV7.

The timeline processing unit 47 performs processing for distributing the generated timeline TL1. The timeline processing unit 47 distributes the generated timeline TL1 to the mobile terminals 12 of a plurality of rescuers P2 who have received the rescue request notification. Thus, the timeline processing unit 47 functions as a timeline distribution unit. For the distributed timeline TL1, it is possible to register or view the initial rescue information through the timeline selection screen 58. If the initial rescue information is additionally registered in the timeline TL1, the timeline processing unit 47 updates the timeline TL1 in the timeline DB 74, and distributes the updated timeline TL1 to the mobile terminal 12.

In addition, the timeline processing unit 47 functions as a timeline transition unit that performs transition processing for transmitting the timeline TL1. The transition processing is processing for transmitting the timeline TL1 to a server, which manages a different timeline, so that the server takes over the timeline TL1.

Figure 10:
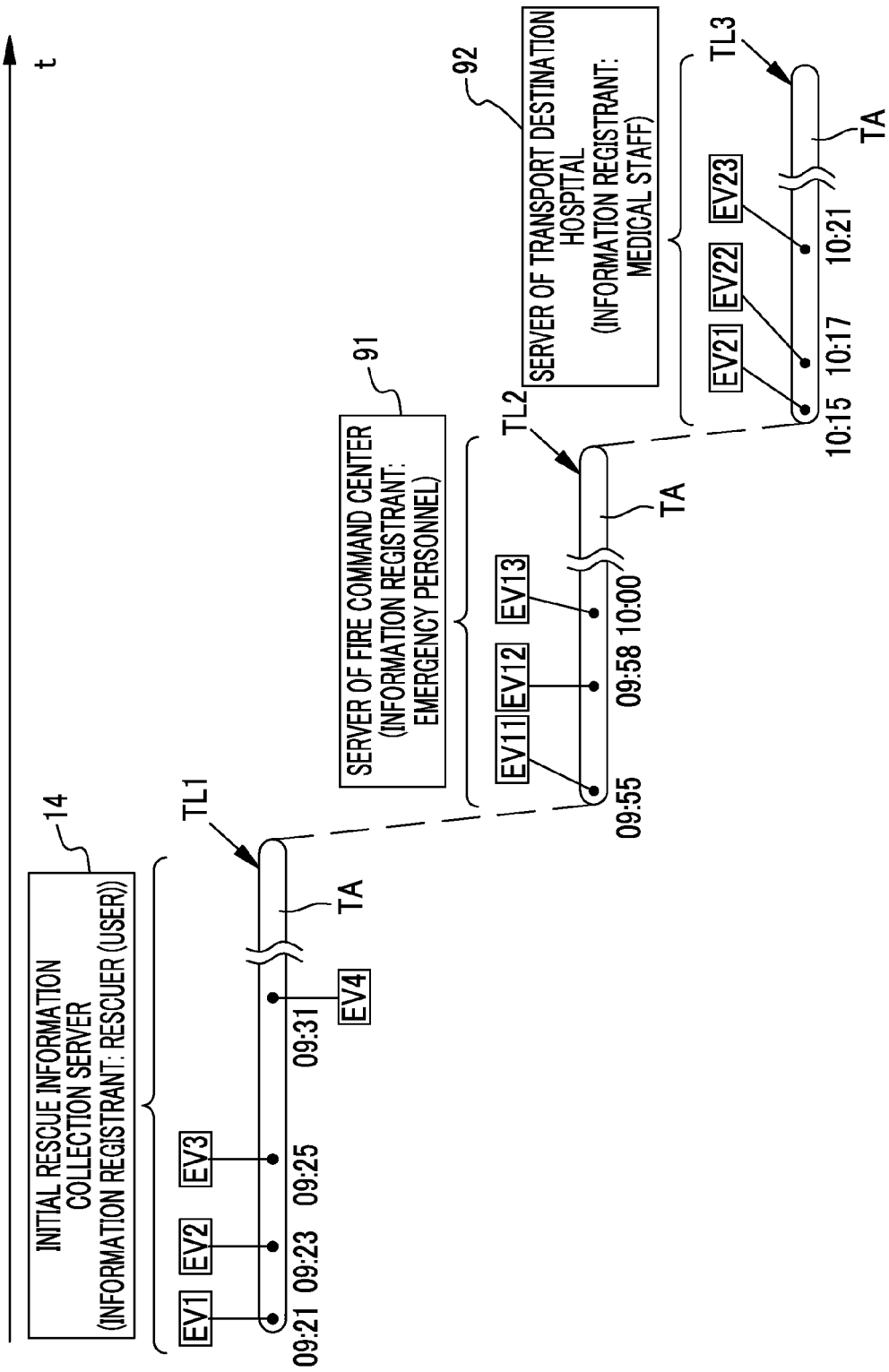
FIG. 10 is an explanatory diagram showing an example of transition of the timeline in each server.

As shown in FIG. 10, initial rescue information in the initial stage before the arrival of emergency personnel who are healthcare workers is registered in the timeline TL1 generated by the information collection server 14. An information registrant is the rescuer P2.

However, for example, when the emergency services 17 arrive, the rescue of the rescue requester P1 transitions from the initial stage before the arrival of the emergency personnel who are healthcare workers to the emergency stage in which rescue work is performed by the emergency personnel. In the emergency stage, for example, another timeline TL2 is generated in a server 91 of the fire command center 16. In the timeline TL2, rescue information in the emergency stage in which rescue work for the rescue requester P1 is performed by the emergency personnel is registered as events (EV11, EV12, . . . ). A person who registers the information in the server 91 is emergency personnel. Examples of the rescue information in the emergency stage are measurement of vital signs, triage treatment, and the like.

In a case where the rescue requester P1 has been transported to the hospital 19 that is a transport destination, another timeline TL3 is generated in a server 92 in the hospital 19. In the timeline TL3, rescue information in the hospital stage in which an operation is performed on the rescue requester P1 by the medical staff of the hospital 19 is registered as events (EV21, EV22, and EV23). A person who registers the information in the server 92 is medical staff. The rescue information in the hospital stage is an emergency surgery or the like. Here, the rescue information recorded in the timeline TL2 or the timeline TL3 is information regarding medical procedures, which are performed by emergency personnel or medical staff who is a healthcare worker, after the arrival of the emergency personnel.

Thus, in a case where a plurality of timelines are generated for one rescue requester P1, it is preferable that the plurality of timelines are managed collectively. The transmission processing is processing for transmitting the timeline TL1 in the initial rescue stage generated in the information collection server 14 to the server 91 of the fire command center 16 or the server 92 of the hospital 19 that is a transport destination. The information collection server 14 transmits the timeline TL1 to a request source in response to the timeline acquisition request from each of the servers 91 and 92.

Figure 11:
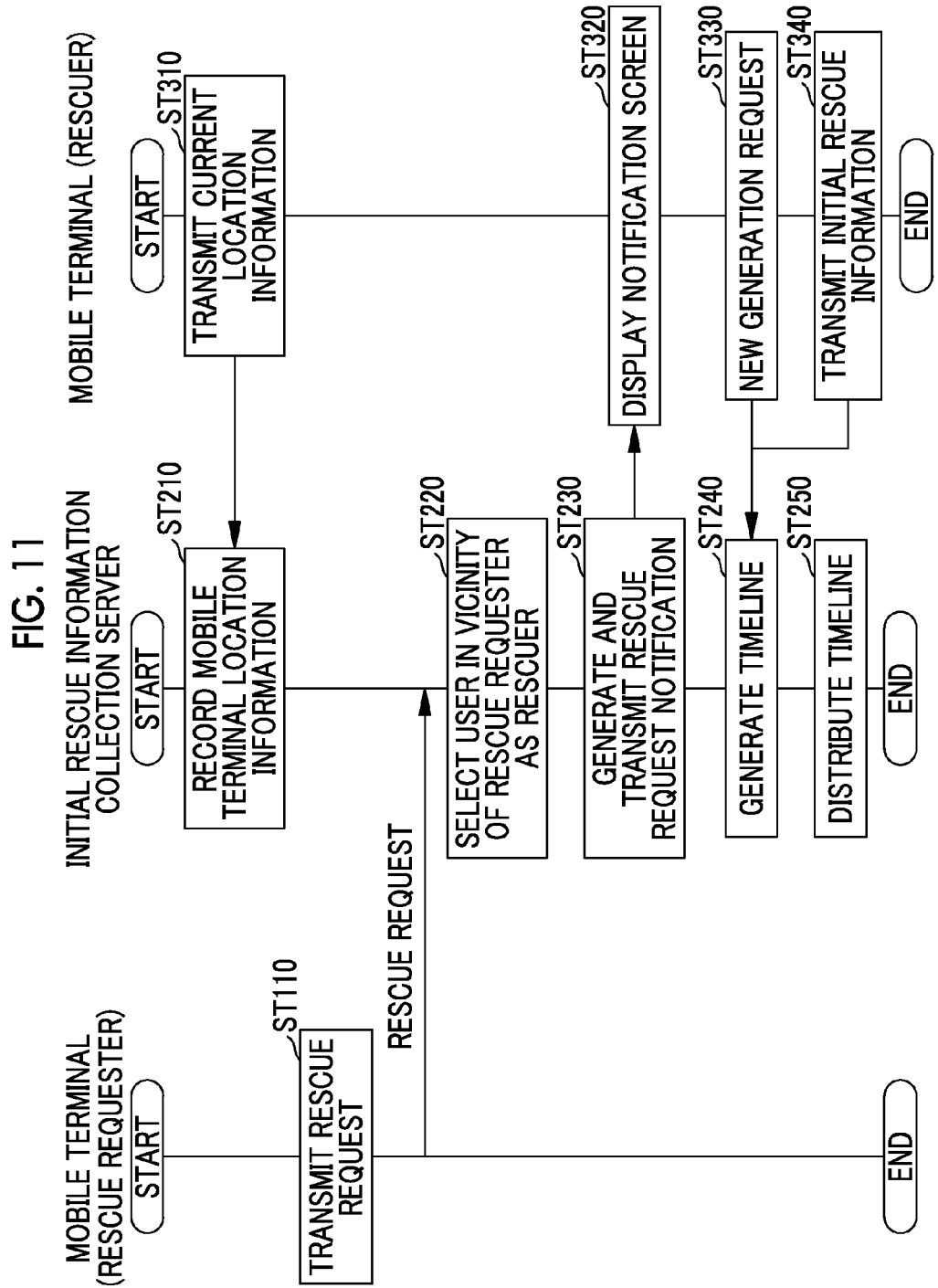
FIG. 11 is a flowchart showing the entire process of the initial rescue information collection system.

Hereinafter, the operation based on the above configuration will be described with reference to the flowchart shown in FIG. 11. The information collection server 14 acquires current location information, which is periodically transmitted from the mobile terminals 11 and 12 of registered users, and records the current location information in the storage device 23B (ST210 and ST310).

In a case where an emergency has occurred in a user and the user has become the rescue requester P1, the client program AP 30A is started in the mobile terminal 11. Then, when the rescue request button 53 is operated on the start screen 52 shown in FIG. 4, a rescue request is transmitted to the information collection server 14 by the rescue request transmission unit 34 of the mobile terminal 11 (ST110).

When the rescue request is received, the information collection server 14 transmits an emergency notification including the current location of the rescue requester P1, who has transmitted the rescue request, to the fire command center 16. When the emergency notification is received, the fire command center 16 dispatches the emergency services 17 to the field of emergency 18.

In the information collection server 14, the map information generation unit 45 generates the map information 49. The map information generation unit 45 selects a user in the vicinity of the rescue requester P1 as the rescuer P2 based on the current location of the rescue requester P1 (ST220). Then, the map information 49 is generated by mapping the current locations of the rescue requester P1 and the rescuer P2. The rescue request notification transmission unit 46 transmits a rescue request notification including the map information 49 to the user selected as the rescuer P2 (ST230). In the mobile terminal 12 of the rescuer P2, the rescue request notification screen 61 is displayed when the rescue request notification is received (ST320).

The rescuer P2 who has received the rescue request notification performs initial rescue work for the rescue requester P1 in the field of emergency 18 where the rescue requester P1 is present. In this case, in order to record initial rescue information before the emergency services 17 arrive, the rescuer P2 transmits the initial rescue information to the information collection server 14 through the mobile terminal 12. The rescuer P2 starts the client program AP 30A in the mobile terminal 12, and operates the TL registration button 54 on the start screen 52 shown in FIG. 5.

In a case where there is no timeline TL1 under registration, the rescuer P2 operates the new generation button 59 on the timeline selection screen 58. Then, a new generation request is transmitted to the information collection server 14 from the mobile terminal 12 (ST330). The information collection server 14 generates a new timeline in response to the new generation request (ST240). The newly generated timeline TL1 is displayed on the timeline selection screen 58 as a timeline under registration. In a case where there is already a timeline TL1 under registration, the timeline TL1 is displayed on the timeline selection screen 58.

As shown in FIGS. 5 and 6, a timeline ID given based on the generation date and time or the address of the field of emergency 18 is displayed in the timeline under registration. The rescuer P2 matches the timeline ID or the address with the current time or the current location while viewing the display, and selects the timeline TL1 corresponding to the field of emergency 18 where the rescuer P2 is present.

In the case of registering initial rescue information, as shown in FIG. 6, a timeline is selected on the timeline selection screen 58, initial rescue information in the format of a text or an image is input through the text input screen 78 or the image input screen 80, and the initial rescue information is transmitted to the information collection server 14 (ST340). The information collection server 14 registers the received initial rescue information in the selected timeline TL1. In this manner, the timeline TL1 is generated and updated (ST240). As described above, initial rescue information is collected from the mobile terminals 12 of a plurality of rescuers P2, and the collected initial rescue information is registered in the timeline TL1.

The generated timeline TL1 is distributed to the mobile terminals 12 of the plurality of rescuers P2 to whom the rescue request notification has been transmitted (ST250). The distributed timeline TL1 can be viewed through the timeline selection screen 58.

As the initial rescue information, as shown in FIG. 9, the condition of the rescue requester, such as the state of breathing or the condition of the rescue requester at the time of the onset of disease, or information regarding the initial rescue procedures performed by the rescuer P2, such as artificial respiration or AED treatment, is registered as the event EV.

By generating the timeline TL1, after the emergency stage in which the emergency personnel have arrived, a healthcare worker can check the initial rescue information before the emergency stage. In the timeline TL1, the event EV that is the initial rescue information is recorded in time series. Therefore, through the timeline TL1, in which order the initial rescue procedures and the like have occurred can be seen. Based on the timeline TL1, a healthcare worker who performs medical procedures on the rescue requester P1 can look back on the initial rescue procedures or the like later. Since the initial symptoms of the rescue requester P1, onset time, and the like are very important information for the medical treatment, the timeline TL1 is useful for the appropriate medical treatment. Therefore, the information collection server 14 that generates the timeline TL1 is very useful in the medical field.

The timeline TL1 can also be viewed through the mobile terminal of a healthcare worker in response to a request from the healthcare worker, such as emergency personnel or medical staff. In addition, the timeline processing unit 47 can perform timeline TL1 transmission processing for transmitting the generated timeline TL1 in response to the acquisition request from the fire command center 16 or each of the servers 91 and 92 of the hospital 19 that is a transport destination. Therefore, since it is possible to integrate the timeline TL1 with the timelines TL2 and TL3 generated separately in the fire command center 16 or the hospital 19, management is easy.

In this example, the timeline processing unit 47 functions as an information receiving unit that receives initial rescue information. However, the initial rescue information may be information regarding at least one of the condition of the rescue requester P1 in the initial stage and the initial rescue procedures performed on the rescue requester P1 in the initial stage before the arrival of emergency personnel who are healthcare workers.

Second Embodiment

Figure 12:
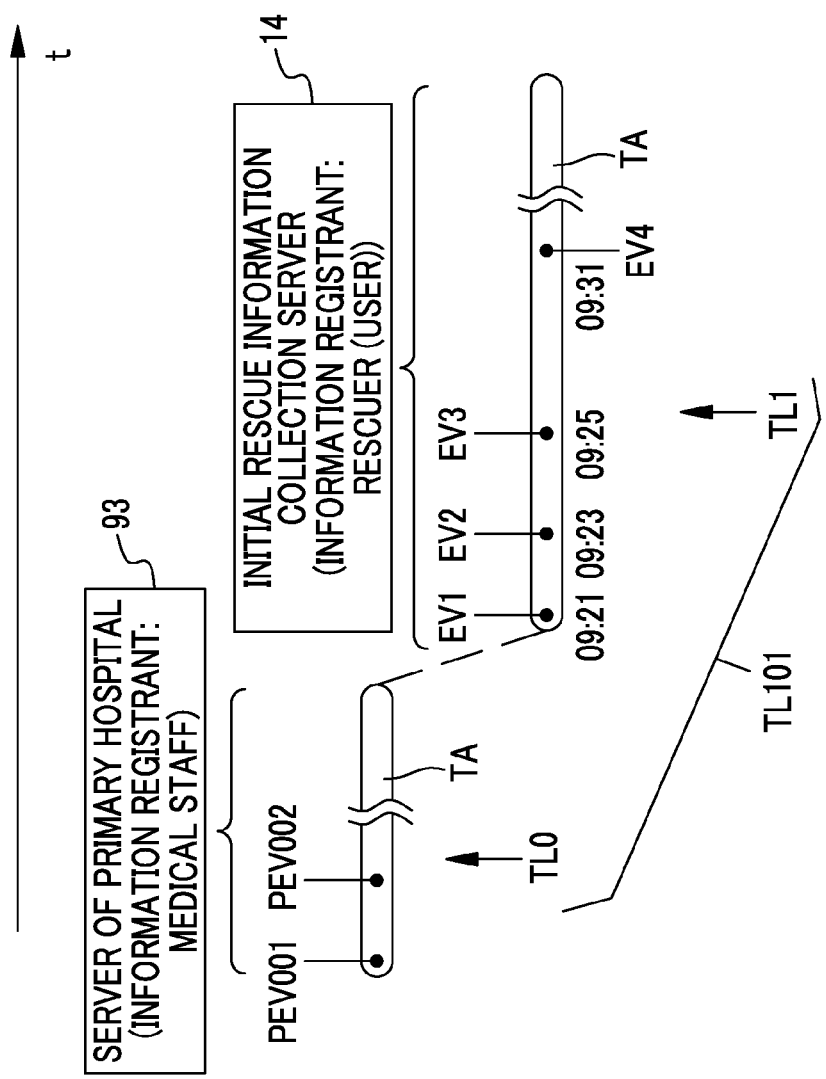
FIG. 12 is an explanatory diagram showing an integrated timeline of another embodiment that is integrated with the timeline of a primary hospital.
Figure 13:
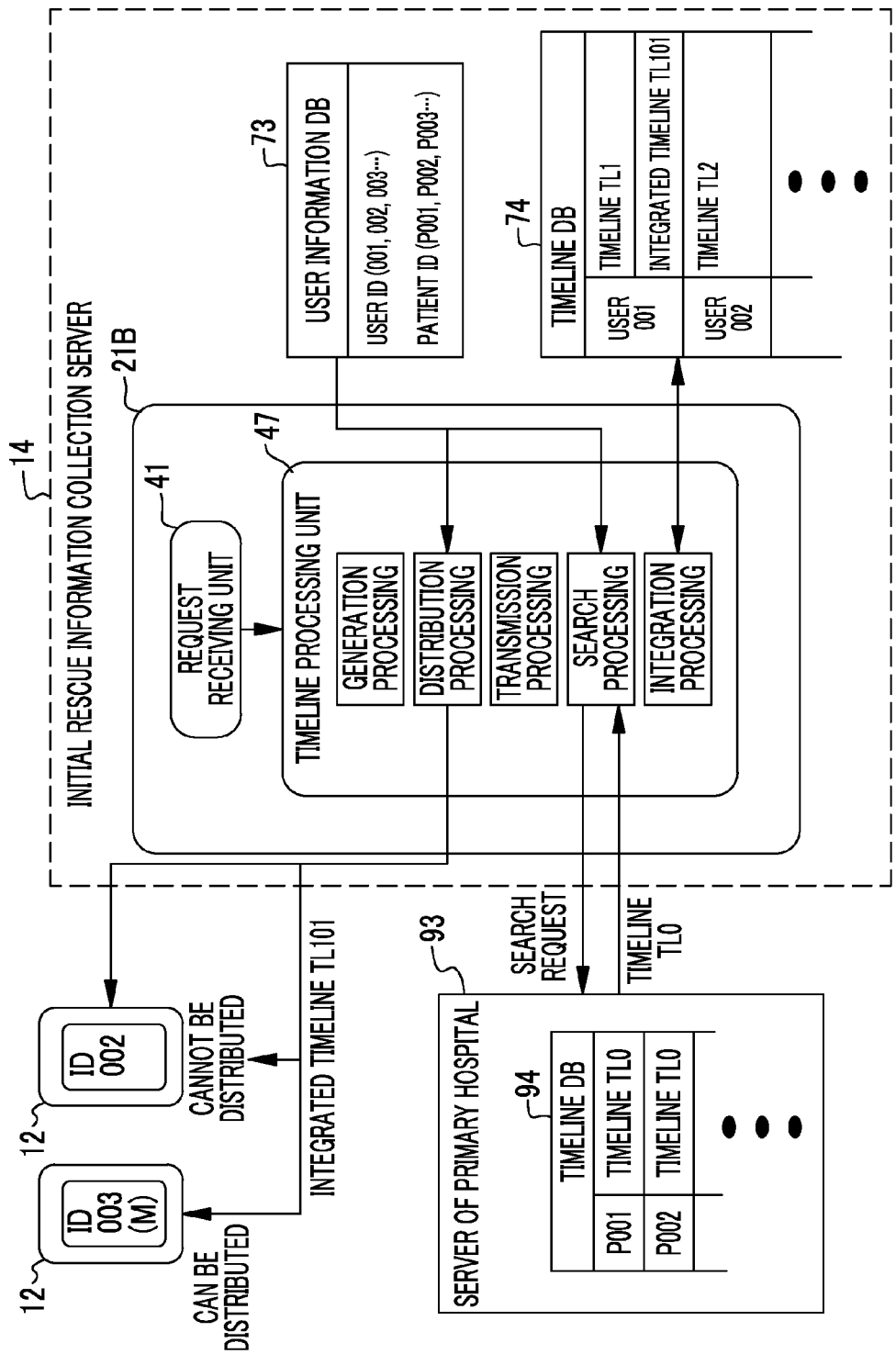
FIG. 13 is a functional block diagram of each server that searches for a timeline at the time of medical treatment in a primary hospital and integrates the timeline with the initial rescue information timeline.

In a second embodiment shown in FIGS. 12 and 13, a past timeline TL0 in which past medical history (PEV001 and PEV002) of the rescue requester P1 is recorded is searched for based on the ID for identifying the rescue requester P1, and the searched timeline TL0 is integrated with the timeline TL1 in which initial rescue information is recorded. Since the other portions are the same as in the first embodiment, the following explanation will be focused on differences. The same portions as in the first embodiment are denoted by the same reference numerals.

As shown in FIG. 12, before the timeline TL1 of the rescue requester P1 is generated, there are cases where the past timeline TL0 of the rescue requester P1 is stored in a server 93 of the primary hospital of the rescue requester P1. If it is possible to acquire the past timeline TL0 and provide emergency personnel or a hospital as a transport destination with the timeline TL0 in addition to the timeline TL1, it is possible to provide more useful information upon subsequent medical treatment for the rescue requester P1.

Therefore, as shown in FIG. 13, in the information collection server 14 of the second embodiment, the timeline processing unit 47 functions as a timeline search unit that searches for the timeline TL0 and a timeline integration unit that integrates the searched timeline TL0 with the timeline TL1.

A patient ID of the primary hospital of the rescue requester P1 or the hospital name or the hospital ID of the primary hospital is recorded in the user information DB 73. In a case where a rescue request is received, the timeline processing unit 47 reads the patient ID and the hospital ID from the user information of the rescue requester P1. Then, a search request including the read patient ID as a search key is generated, and a timeline TL0 search request is transmitted to the server 93 of the hospital specified by the read hospital ID.

The server 93 of the primary hospital has a timeline DB 94 in which the timeline TL0 of a plurality of patients is stored. When a search request is received from the information collection server 14, the server 93 searches for the timeline TL0 of the corresponding patient ID from the timeline DB 94. Then, in a case where there is a corresponding timeline TL0, the timeline TL0 is transmitted to the information collection server 14 that is a request source.

The timeline processing unit 47 generates an integrated timeline TL101 by integrating the received timeline TL0 with the timeline TL1 of the corresponding rescue requester P1. The integrated timeline TL101 is stored in the timeline DB 74.

The timeline processing unit 47 can transmit the integrated timeline TL101 in response to the request from the server 91 of the fire command center 16 or the server 92 at the transport destination.

In addition, the integrated timeline TL101 may be distributed to the mobile terminal 12 of the rescuer P2, so that the rescuer P2 views the integrated timeline TL101. In a case where the timeline TL1 is integrated with the past timeline TL0, it is preferable that the timeline processing unit (timeline distribution unit) 47 distributes the integrated timeline TL101 only to the rescuer P2 who is a user registered as a healthcare worker in advance. That is, it is preferable that a user to whom the integrated timeline TL101 is to be distributed is limited to a user registered as a healthcare worker in advance.

This is because the past medical history of the rescue requester P1 is included in the integrated timeline TL101 and the past medical history includes highly confidential information relevant to the privacy of the rescue requester P1. Since the rescuer P2 is a user who happens to be close to the rescue requester P1, people who are not healthcare workers are also included. For this reason, it is not preferable for people who are not healthcare workers to view the past medical history of the rescue requester P1.

Therefore, when distributing the integrated timeline TL101, the timeline processing unit 47 checks whether or not the rescuer P2, who is a user at the distribution destination, is registered as a healthcare worker in advance with reference to the user information DB 73, and distributes the integrated timeline TL101 only to the rescuer P2 registered as a healthcare worker. In FIG. 13, since the rescuer P2 having a user ID of "002" is not a healthcare worker, the integrated timeline TL101 is not distributed to the mobile terminal 12. On the other hand, since the rescuer P2 having a user ID of "003" is a healthcare worker (shown by "M"), the integrated timeline TL101 is distributed to the mobile terminal 12.

In this example, an example has been described in which there is only one primary hospital of the rescue requester P1. However, in a case where there is a plurality of hospitals, the timeline TL0 may be acquired from the plurality of servers 93. In this example, an example has been described in which the patient ID of the primary hospital of the rescue requester P1 can be specified from the user information 48. However, in a case where the patient ID cannot be specified, my number scheduled to be introduced in the future may be used as a search key. In this case, the timeline processing unit 47 of the information collection server 14 transmits a search request including my number as a search key to the servers 93 of a plurality of unspecified hospitals. The server 93 that has received the search request searches for the corresponding timeline TL0 with my number as a search key. In a case where there is a corresponding timeline TL0, the timeline TL0 is transmitted to the information collection server 14 as a search result.

Third Embodiment

In a third embodiment shown in FIG. 14, the information collection server 14 has a function of receiving information from a biological sensor 96 that the rescue requester P1 is wearing. The biological sensor 96 is, for example, a heart rate sensor, a respiration sensor, or a skin impedance sensor. The biological sensor 96 outputs measurement information, such as a heart rate or a respiratory rate. For example, measurement information output from the biological sensor 96 is wirelessly transmitted to the mobile terminal 11 of the rescue requester P1. The mobile terminal 11 transmits the measurement information received from the biological sensor 96 to the information collection server 14 using the information registration function of the client program AP 30A. The information collection server 14 registers the received measurement information in the timeline TL1 as MI10 and MI11.

According to this, since it is possible to collect the biometric information of the rescue requester P1 in the initial rescue stage, the usability of the timeline TL1 is further improved.

In the embodiments described above, the management entity of the information collection server 14 or application services for initial rescue information collection may be a private enterprise, or may be a public entity, such as a local government. Alternatively, medical facilities, such as the hospital 19, may be the management entity. In addition, public agencies, such as the fire command center 16, may be the management entity.

The hardware configuration of the information collection server 14 may be modified in various ways. For example, in order to improve the processing capacity or reliability, the information collection server 14 may be formed by a plurality of server computers that are separate hardware components. Thus, the hardware configuration of the computer system can be appropriately changed according to the required performance, such as capacity, safety, or reliability. Without being limited to hardware, in order to ensure the safety or reliability, a program may be duplicated or may be stored so as to be distributed in a plurality of storage devices.

It is needless to say that the invention is not limited to the embodiments and modifications described above and various configurations can be adopted without departing from the scope of the invention. For example, the embodiments and modifications described above can be appropriately combined. In addition to the program, the invention also extends to a storage medium for storing the program.

What is claimed is:

1. An initial rescue information collection device, comprising:
   a rescue request receiving unit that receives a rescue request;
   a rescue request notification transmission unit that selects users, who are present in a predetermined distance range from a current location of a rescue requester who has sent the rescue request, among users registered in advance and transmits a rescue request notification to the selected users;
   an information receiving unit that receives information from mobile terminals of the users who have received the rescue request notification and that receives initial rescue information after the rescue request notification, the initial rescue information being information regarding at least one of initial rescue procedures performed on the rescue requester in an initial stage before arrival of emergency personnel who are healthcare workers or a condition of the rescue requester in the initial stage;
   a timeline generation unit that generates a timeline in which the initial rescue information is recorded in time series,
   wherein the timeline includes a visually depicted time axis and on which information includes the initial rescue information is indicated in time series, and a timeline transition unit that performs transition of the timeline, in which the initial rescue information is recorded, to a server that manages another timeline in which medical procedures performed on the rescue requester by the healthcare workers after arrival of the emergency personnel is recorded.

2. The initial rescue information collection device according to claim 1, further comprising:
a timeline distribution unit that distributes the timeline to the mobile terminals of the plurality of users who have received the rescue request notification.

3. The initial rescue information collection device according to claim 1, further comprising:
a mobile terminal current location acquisition unit that acquires current locations of mobile terminals of the users including a transmission source of the rescue request,
wherein the rescue request notification transmission unit selects the users, to whom the rescue request notification is to be transmitted, from the current locations of the mobile terminals.

4. The initial rescue information collection device according to claim 2, further comprising:
a mobile terminal current location acquisition unit that acquires current locations of mobile terminals of the users including a transmission source of the rescue request,
wherein the rescue request notification transmission unit selects the users, to whom the rescue request notification is to be transmitted, from the current locations of the mobile terminals.

5. The initial rescue information collection device according to claim 2, further comprising:
a timeline transmission unit that transmits the timeline, in which the initial rescue information is recorded, to a server that manages another timeline in which medical procedures performed on the rescue requester by the healthcare workers after arrival of the emergency personnel is recorded.

6. The initial rescue information collection device according to claim 3, further comprising:
a timeline transmission unit that transmits the timeline, in which the initial rescue information is recorded, to a server that manages another timeline in which medical procedures performed on the rescue requester by the healthcare workers after arrival of the emergency personnel is recorded.

7. The initial rescue information collection device according to claim 1, further comprising:
a timeline search unit that searches for a past timeline, in which past medical history of the rescue requester is recorded, based on an ID for identifying the rescue requester; and
a timeline integration unit that integrates the timeline in which the initial rescue information is recorded with the past timeline.

8. The initial rescue information collection device according to claim 2, further comprising:
a timeline search unit that searches for a past timeline, in which past medical history of the rescue requester is recorded, based on an ID for identifying the rescue requester; and
a timeline integration unit that integrates the timeline in which the initial rescue information is recorded with the past timeline.

9. The initial rescue information collection device according to claim 3, further comprising:

a timeline search unit that searches for a past timeline, in which past medical history of the rescue requester is recorded, based on an ID for identifying the rescue requester; and
a timeline integration unit that integrates the timeline in which the initial rescue information is recorded with the past timeline.

10. The initial rescue information collection device according to claim 4, further comprising:
a timeline search unit that searches for a past timeline, in which past medical history of the rescue requester is recorded, based on an ID for identifying the rescue requester; and
a timeline integration unit that integrates the timeline in which the initial rescue information is recorded with the past timeline.

11. The initial rescue information collection device according to claim 5,
wherein, in a case where the past timeline is integrated with the timeline in which the initial rescue information is recorded, the timeline distribution unit distributes the timeline only to a user registered as a healthcare worker in advance.

12. The initial rescue information collection device according to claim 1,
wherein the information receiving unit receives at least one of a still image, a motion picture, or a text as the initial rescue information.

13. The initial rescue information collection device according to claim 2,
wherein the information receiving unit receives at least one of a still image, a motion picture, or a text as the initial rescue information.

14. The initial rescue information collection device according to claim 3,
wherein the information receiving unit receives at least one of a still image, a motion picture, or a text as the initial rescue information.

15. The initial rescue information collection device according to claim 1,
wherein the information receiving unit receives information from a biological sensor that the rescue requester is wearing.

16. The initial rescue information collection device according to claim 2,
wherein the information receiving unit receives information from a biological sensor that the rescue requester is wearing.

17. An operation method of an initial rescue information collection device, comprising:
a rescue request receiving step of receiving a rescue request from a rescue requester who has sent the rescue request;
a rescue request notification transmission step of selecting users, who are present in a predetermined distance range from a current location of the rescue requester, among users registered in advance and transmitting a rescue request notification to the selected users;
an information receiving step of receiving information from mobile terminals of the users who have received the rescue request notification, initial rescue information regarding at least one of initial rescue procedures performed on the rescue requester before arrival of emergency personnel who are healthcare workers or a condition of the rescue requester being received after the rescue request notification;

a timeline generation step of generating a timeline in which the initial rescue information is recorded in time series, wherein the timeline includes a visually depicted time axis and on which information includes the initial rescue information is indicated in time series, and a timeline transition step that performs transition of the timeline, in which the initial rescue information is recorded, to a server that manages another timeline in which medical procedures performed on the rescue requester by the healthcare workers after arrival of the emergency personnel is recorded.

18. A non-transitory computer readable computer medium storing an initial rescue information collection program causing a computer to execute:

a rescue request receiving step of receiving a rescue request from a rescue requester who has sent the rescue request;

a rescue request notification transmission step of selecting users, who are present in a predetermined distance range from a current location of the rescue requester, among users registered in advance and transmitting a rescue request notification to the selected users;

an information receiving step of receiving information from mobile terminals of the users who have received the rescue request notification, initial rescue information regarding at least one of initial rescue procedures performed on the rescue requester before arrival of emergency personnel who are healthcare workers or a condition of the rescue requester being received after the rescue request notification;

a timeline generation step of generating a timeline in which the initial rescue information is recorded in time series, wherein the timeline includes a visually depicted time axis and on which information includes the initial rescue information is indicated in time series, and a timeline transition step that performs transition of the timeline, in which the initial rescue information is recorded, to a server that manages another timeline in which medical procedures performed on the rescue requester by the healthcare workers after arrival of the emergency personnel is recorded.

19. An initial rescue information collection system, comprising:

a mobile terminal; and an initial rescue information collection device that is able to communicate with the mobile terminal through a network, wherein the initial rescue information collection device comprises:

a rescue request receiving unit that receives a rescue request from a rescue requester who has sent the rescue request;

a rescue request notification transmission unit that selects users, who are present in a predetermined distance range from a current location of a rescue requester, among users registered in advance and transmits a rescue request notification to the selected users;

an information receiving unit that receives information from the mobile terminals of the users who have received the rescue request notification and that receives initial rescue information regarding at least one of initial rescue procedures performed on the rescue requester before arrival of emergency personnel, who are healthcare workers, or a condition of the rescue requester after the rescue request notification;

a timeline generation unit that generates a timeline in which the initial rescue information is recorded in time series, wherein the timeline includes a visually depicted time axis and on which information includes the initial rescue information is indicated in time series, and a timeline transition unit that performs transition of the timeline, in which the initial rescue information is recorded, to a server that manages another timeline in which medical procedures performed on the rescue requester by the healthcare workers after arrival of the emergency personnel is recorded.

* * * * *